United States Patent [19]

Fulmer

[11] Patent Number: 4,567,304
[45] Date of Patent: * Jan. 28, 1986

[54] PROCESS FOR PREPARING ACETONE AND PHENOL

[75] Inventor: John W. Fulmer, Mt. Vernon, Ind.

[73] Assignee: General Electric Company, Mt. Vernon, Ind.

[*] Notice: The portion of the term of this patent subsequent to Oct. 30, 2001 has been disclaimed.

[21] Appl. No.: 614,124

[22] Filed: May 24, 1984

Related U.S. Application Data

[63] Continuation-in-part of Ser. No. 482,298, Apr. 5, 1983, Pat. No. 4,480,134.

[51] Int. Cl.$^4$ ............................................. C07C 45/53
[52] U.S. Cl. ..................................... 568/385; 568/798
[58] Field of Search ............................... 568/385, 798

[56] References Cited

U.S. PATENT DOCUMENTS

| | | | |
|---|---|---|---|
| 2,715,145 | 8/1955 | Bewley et al. | 568/385 |
| 2,728,798 | 12/1955 | Armstrong et al. | 568/385 |
| 2,737,480 | 3/1956 | Adams et al. | 568/385 |
| 2,781,222 | 4/1959 | Joris et al. | 568/385 |
| 2,904,592 | 9/1959 | Ellis et al. | 568/385 |
| 2,906,789 | 9/1959 | McNaughton | 568/385 |
| 2,957,921 | 10/1960 | Adams et al. | 568/385 |
| 2,986,583 | 5/1961 | Robbers et al. | 568/385 |
| 3,215,745 | 11/1965 | Frank | 568/385 |
| 4,271,322 | 6/1981 | Matsunoga et al. | 568/385 |
| 4,351,967 | 9/1982 | Nishimura et al. | 568/798 |

Primary Examiner—James H. Reamer
Attorney, Agent, or Firm—Martin B. Barancik

[57] ABSTRACT

Benzene, toluene and ethylbenzene is removed from the heavy residues of a phenol distillation in a phenol and acetone from cumene process.

8 Claims, 2 Drawing Figures

PROCESS FOR PREPARING ACETONE AND PHENOL

This application is a continuation-in-part of copending application Ser. No. 482,298, filed Apr. 5, 1983 now U.S. Pat. No. 4,480,134.

BACKGROUND OF THE INVENTION

Phenol is a basic commodity chemical with many end uses. Most of the phenol manufactured is prepared from isopropyl benzene, hereafter referred to as cumene. The reaction sequence is short and entails the following steps:

1. Air oxidation of cumene to give cumene hydroperoxide.

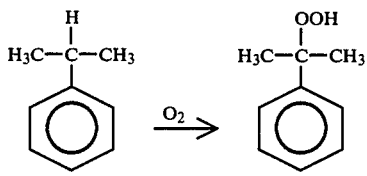

2. Acid cleavage of the hydroperoxide to provide phenol and acetone.

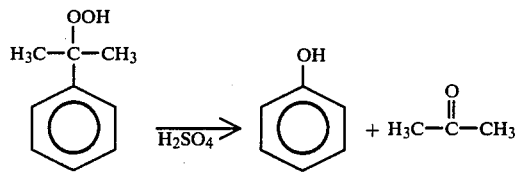

The phenol and acetone are separated and each one purified to the degree necessary to satisfy its ultimate use. As is readily observed, for every mole of phenol that is produced, a mole of acetone is also theoretically produced. Acetone is also a commodity chemical with various end uses. Although not shown in the schematic equations, there are by-products formed as well which must be removed to various degrees depending upon the end use of the phenol or acetone. Additionally, other by-products are formed by various concentrating methods and processing conditions utilized after the cleavage of the cumene hydroperoxide. The by-products include dimethylbenzyl alcohol, α-methylstyrene, cumylphenol, mesityl oxide, hydroxy acetone, benzene, toluene, ethylbenzene, dimers and higher polymers of various components including α-methylstyrene.

Various of these heavier tar like materials, for example the above mentioned polymers, generally known as "heavy ends", are removed as residues from the bottoms of a distillation tower utilized to purify the phenol. Since many of these "heavy ends" are made from products desirable for recycle such as cumene and α-methylstyrene, as well as cumyl phenol, it has become part of the general processing steps of phenol manufacture to break down these heavy ends through, for example, a heat treatment, "cracking", to their individual desirable compounds such as cumene. These compounds are then recycled into the process streams thereby increasing the overall conversion of the process. However in accomplishing this desirable effect, the heat treatment also produced other products which had undesirable effects on product purity and process economics when introduced into the process streams on recycle. The production of these undesirable compounds by the heat treatment has not been appreciated to date. Specifically the cracking of the heavy ends to moieties including benzene, toluene and ethylbenzene places impurities into the acetone which are extremely difficult if not impossible to economically remove during the acetone purification. The presence of benzene in product acetone removes certain end use markets from consideration. Therefore, an acetone product with a substantially reduced benzene content is a desirable goal. The presence of ethylbenzene further downstream in the distillation train brings about poorer process economics when its removal is performed by prior art methods.

Better acetone quality and improved process economics have been achieved by removal of the benzene, toluene and ethylbenzene through the method of this invention. Not only are the advantages of my earlier copending application Ser. No. 482,298, filed Apr. 5, 1983 and herein incorporated by reference maintained, but additional advantages are observed. Efficient removal of ethylbenzene occurs with very little loss of cumene. Moreover, a more efficient separation of cumene from butyl benzenes surprisingly occurs further down the distillation train as a result of the fact that most of the ethylbenzene has already been removed. Surprisingly it has also been noticed that compounds which deleteriously affect phenol quality according to the sulfonation color test can also be removed from the process by the method of this invention. Previously such compounds had been removed in the phenol purification procedures at a more disadvantageous time, thereby resulting in more product loss and poorer energy utilization. These positive results are achieved with very little loss in overall cumene, the process starting material. In fact, cumene recovery is actually increased and provides further economic justification for an additional separation procedure.

SUMMARY OF THE INVENTION

In accordance with the invention, there is a process for oxidatively preparing phenol and acetone from cumene including the steps of a. cleaving cumene hydroperoxide to produce a mixture comprising phenol, acetone and side products including heavy residue;

b. separating acetone from phenol and heavy residue;

c. separating the heavy residue from the phenol;

d. treating the said heavy residue at elevated temperature;

e. separating lighter boiling material from heavier boiling material of the heavy residue, said lighter boiling material comprising cumene, α-methylstyrene, and phenol;

f. separating the said lighter boiling material into two fractions, the lighter fraction comprising the bulk of the benzene, toluene, and ethylbenzene, the heavier fraction comprising the bulk of the phenol, cumene and α-methylstyrene and g. not recycling into the process streams any significant portion of the said lighter fraction.

A further aspect of the invention is the materials which may be found in the said lighter boiling fraction that adversely affect the phenol quality as measured by the sulfonation color test. These materials, generally thought to include lighter boiling carbonyl compounds, are separated with the benzene, toluene and ethylbenzene and may no longer enter the recycle processes in substantial quantity. It should be noted that since the boiling of ethylbenzene is substantially higher than both benzene and toluene, the separation of ethylbenzene from higher boiling materials brings about the almost total separation of benzene and toluene as well.

DETAILED DESCRIPTION OF THE INVENTION

As stated previously, the conversion of cumene to phenol and acetone is a well known process utilizing individual process steps well known in the industry. The formation of the cumene hydroperoxide by the air oxidation of cumene is performed under standard conditions and the cumene hydroperoxide brought to a higher concentration by stripping unreacted cumene. To this concentrated quantity of cumene hydroperoxide is added a catalytic quantity of sulfuric acid which helps bring about the cleavage of cumene hydroperoxide to phenol and acetone. The phenol and acetone is then separated or "split" usually on the basis of their boiling points. Each of the basic values, phenol and acetone, is then purified according to whatever end use purity is required, usually by distillation.

As in virtually all chemical processes, the yield of the desired phenol and acetone is not one hundred percent. Relatively early in the technology it was realized that the residue of the initial distillation from the phenol purification, or "heavy ends", were relatively rich in materials, for example, dimers and polymers of α-methylstyrene, cumylphenol and the like which would provide cumene, cumene precursors and phenol after an economic "cracking" reaction, see U.S. Pat. No. 2,715,145 incorporated by reference. Such cumene could eventually be recovered and recycled to the initial oxidation reaction. The recovered phenol would eventually join the phenol in the product purification processing stream. The temperature necessary to bring about this decomposition or "cracking" reaction varies according to the composition of the "heavy ends" and the pressure of the reaction; however, generally a temperature substantially above the boiling points of phenol and acetophenone and in the range of from about 200° to 400° C., preferably about 275°-350° C., is employed.

It has been unappreciated until now that the usual cracking conditions are sufficient to not only produce desirable components but are also of sufficient strength to crack the substituted aromatics all the way down to alkyl substituted benzene, i.e. ethylbenzene and toluene, or to remove all substituents from the aromatic molecule and produce benzene. Previously the entire distillate fraction was recycled into the process, the undistilled residue being incinerated. This recycling caused the acetone fraction to be contaminated with benzene and toluene, particularly benzene, and the ethylbenzene to be carried along with the cumene until a relatively expensive, low efficiency separation finally occurred.

It has now been discovered that the benzene and toluene contaminant can be essentially totally removed from product acetone by treating the distillate from the cracker which breaks down the "heavy ends" accompanying the phenol to a further separation. Additionally the removal of the ethylbenzene brings about substantial cumene usage savings in the distillation train, particularly at the separation point of α-methylstyrene and cumene from ethylbenzene. This inventive separation or "topping" is a distillation which separates the benzene, toluene and ethylbenzene from the higher boiling constituents such as the cumene, α-methylstyrene, and phenol. Such topping is effectively accomplished by removing a relatively small amount of the fluid in the overhead, thereby maintaining a substantial amount of the desired materials in the residue which is recycled. This distillate does not enter the recycle stream and is generally incinerated. Any set of distillation conditions and equipment parameters which can accomplish the goal of removing essentially all the benzene and toluene and substantial quantities of the ethylbenzene from the cracker distillate in as small a volume as possible can be employed. Such parameters are well known or easily obtainable to one skilled in chemical engineering.

It has additionally been discovered that this topping of the cracker distillate has the further advantage of generally removing from the recycle stream some of the contaminants which deleteriously affect phenol quality as measured by the sulfonation color test. Previously these contaminants were allowed to build up in the phenol distillation train until they had to be removed with a concurrent decrease in product phenol and an increase in steam usage. Removal of these contaminants in the benzene, toluene and ethylbenzene fraction creates a more efficient process.

A further understanding of the process may be obtained through the study of the Figures attached to this specification.

Cumene enters oxidizer, 12, through line 11 and reacts with air brought in through line 7 to form cumene hydroperoxide. The cumene hydroperoxide is transported from the oxidizer through line 17 to the stripper, 24 wherein the cumene hydroperoxide is concentrated to a higher percent with the concomitant removal of unreacted cumene which is drawn off through line 21 and recycled to line 11 for further use. The concentrated cumene hydroperoxide enters the cleavage reactor, 32, through line 29. A catalytic quantity of sulfuric acid is introduced into the cleavage reactor through line 35 and the cumene hydroperoxide cleaved into a mixture of phenol, acetone and by-products. This mixture is then transported through line 39 to the splitter column, 44, wherein the phenol and acetone are split into two streams by distillation, the overhead containing the acetone and lighter boiling by products leaving the column by line 41 for further purification, the phenol and higher boiling by-products leaving the splitter in line 47 and entering phenol distillation tower, 56. The distilled phenol leaves the distillation tower in line 53 for further purification. The residue, previously described as "heavy ends" is transported to the cracker, 64, by line 59. In the cracker, the temperature and pressure are adjusted so that the heavy ends are decomposed, the residue being transported to the incinerator by line 67 and the distillate comprising the mixture of cumene, α-methylstyrene and phenol being recycled by line 61 to line 39 where it again enters the splitter column, 44. The cumene, α-methylstyrene and any benzene, toluene and ethylbenzene present is separated from the phenol in the splitter column and accompanies the acetone for further purification through line 41 to acetone distillation column 46. Acetone together with benzene is removed in the overheads through line 49 and is further processed to acetone product. The residue from 46 comprising cumene, α-methylstyrene, and toluene and ethylbenzene is brought through line 51 to the α-methylstyrene hydrogenation recovery area, 58, wherein the α-methylstyrene is hydrogenated to cumene. Toluene and ethylbenzene are removed in the overhead in line 55. Butyl benzenes are removed from 58 in the residue by line 81 and combined with the contents of line 55 and are carried to the incinerator, 78, by line 85. Cumene is removed by a side draw and is recycled through line 87 to the oxidizer, 12. However, significant amounts of cumene are lost in both the overhead, line 55, and the residue, line 81.

Figure 1:
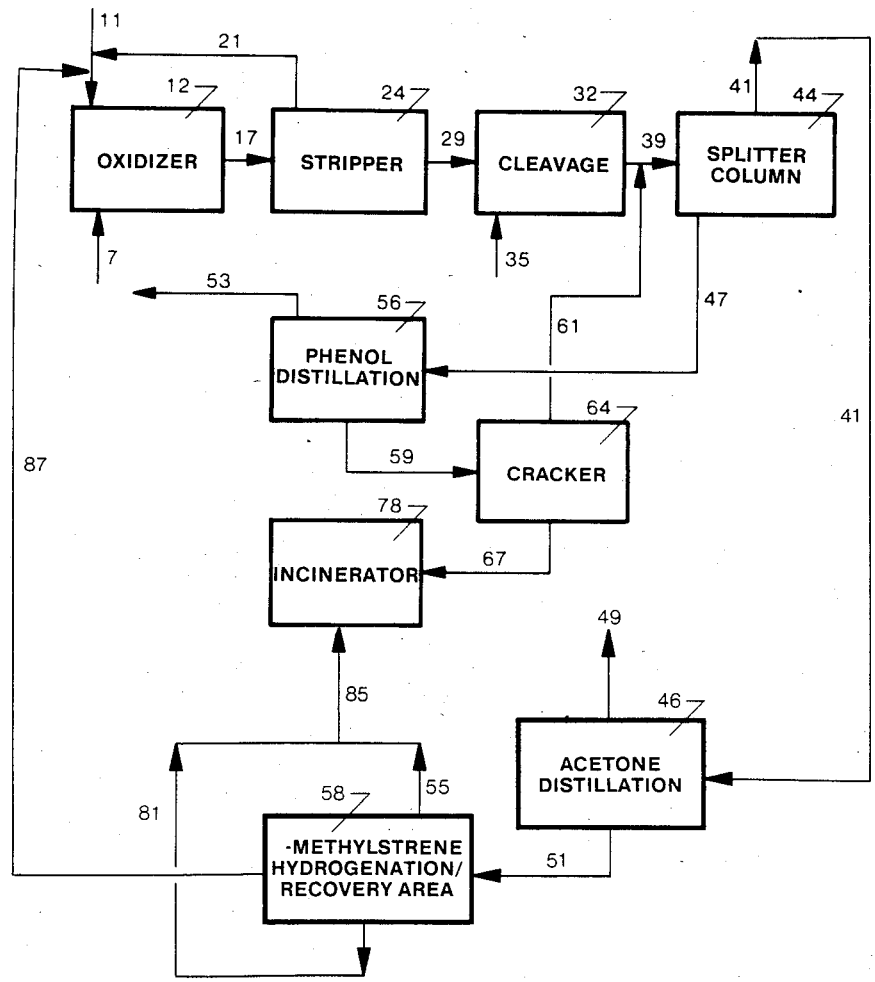
FIG. 1 shows the key steps in the previously practiced process of preparing phenol and acetone from cumene.
Figure 2:
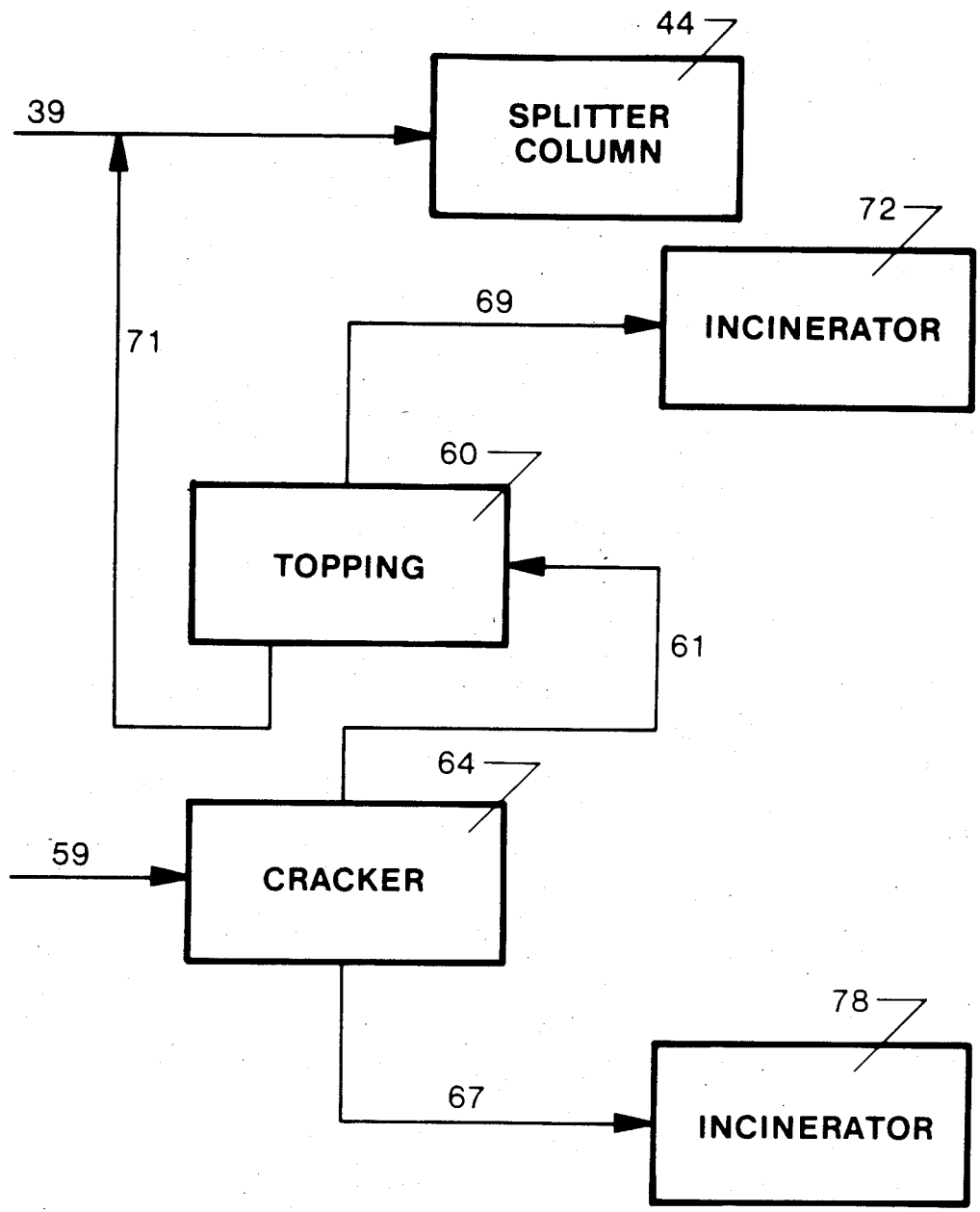
FIG. 2 shows the integration of the topping column of the invention into the previously practiced process steps.

FIG. 2 shows the process of this invention. All process steps are the same through the cracker, 64. However instead of all the cracker distillate being recycled to line 39 by line 61, a topping distillation column, 60, is interposed between the cracker, 64, and line 39. Line 61 feeds the cracker distillate to the topping distillation column, 60, wherein the lighter fraction comprising the benzene, toluene and ethylbenzene is separated from the heavier fraction comprising cumene, α-methylstyrene and phenol. The lighter fraction is not recycled into the process streams but is preferably transported to incinerator 72 by line 69. The heavier fractions are recycled into the process by transporting through line 71 to line 39. Removal of the ethylbenzene here allows for greater recovery of cumene at the α-methylstyrene hydrogenating recovery area. Easier separation occurs between the remaining ethylbenzene and cumene which also allows for lesser cumene lost in the butyl benzene fraction.

In FIG. 2, the topping distillation 60 is shown between the cracker, 64 and line 39. However it need not be present in this particular location as long as the distillate from the cracker is further distilled to remove the benzene, toluene and ethylbenzene prior to the recycling of the cracker distillate material to the main processing stream. Once present with the acetone, the benzene and toluene are extremely difficult if not impossible to separate. Generally a removal by the topping column of about 6–8 wt. percent of the feed is sufficient to remove above about 90 wt. percent, preferably about 95 percent of the ethylbenzene and virtually all of the benzene and toluene. The separation is extremely efficient. It is accompanied by a loss of only about 1–3 percent of the cumene present.

It has also been discovered that the lighter fraction also may contain materials which deleteriously affect the phenol quality as measured by the sulfonation color test.

Below are examples of the invention. These examples are intended to illustrate but not narrow the inventive concept disclosed herein.

EXAMPLE 1

The distillate obtained from cracker, 64, of a commercial phenol plant utilizing cumene as a feed stock was analyzed for various components.

The majority of the distillate was cumene and phenol. The remainder of the distillate was divided into various aromatics and ketonics, some with a boiling point lighter than cumene, others with a boiling point between cumene and phenol. Ketonics were associated with the lighter boiling aromatics. There was 0.08 wt. % benzene, 1.1 wt. % toluene and 4.3 wt. % ethylbenzene in the distillate.

This distillate was then subjected to atmospheric distillation utilizing a twenty tray one inch internal diameter column. The percentage of the cracker distillate which distilled over at the overhead temperature was recorded together with the wt. percent ethylbenzene remaining in the residue as well as the wt. percent cumene present in the overheads. Essentially all of the benzene and toluene were removed from the distillate. Below are the results of the laboratory runs.

| EXPERIMENT | OVERHEAD VAPOR TEMP °C. | SUMP LIQUID TEMP °C. | WT. % DISTILLATE REMOVED | WT. % ETHYLBENZENE REMOVED | WT. % CUMENE REMAINING |
|---|---|---|---|---|---|
|  | 140 | 171 | 8.1 | 94.5 | 98.7 |
| 2 | 140 | 171 | 5.6 | 95.5 | 98.2 |
| 3 | 137 | 170 | 7.0 | 93.6 | 98.7 |

The data clearly show that ethylbenzene can be effectively removed by topping the cracker distillate. Virtually all of the benzene and toluene are also removed with the accompanying advantages. This removal was accomplished while retaining virtually all the cumene for effective recycle. Prior to this invention, ethylbenzene was removed from the system at the α-methylstyrene hydrogenation/recovery area of the plant in a separation of the ethylbenzene from a stream comprising ethylbenzene, cumene, α-methylstyrene and butyl benzenes. However, this was a relatively inefficient step and substantial amounts of cumene were intermixed with the ethylbenzene as well. Following the new process of this invention, very little cumene is lost to either the overhead residual ethylbenzene or the bottom butyl benzenes.

What is claimed is:
1. A process for oxidatively preparing phenol and acetone from cumene including the steps of
   a. cleaving cumene hydroperoxide to produce a mixture comprising phenol, acetone and side products including heavy residue;
   b. separating acetone from phenol and heavy residue;
   c. separating the heavy residue from the phenol;
   d. treating the said heavy residue at elevated temperature;
   e. separating lighter boiling material from heavier boiling material of the residue, said lighter boiling material comprising cumene, α-methylstyrene, and phenol;
   f. separating the said lighter boiling material into two fractions, the lighter fraction comprising the bulk of benzene, toluene and ethylbenzene, the heavier fraction comprising the bulk of the phenol, cumene and α-methylstyrene; and
   g. not recycling into the process streams any significant portion of the said lighter fraction.
2. A process in accordance with claim 1 wherein the said lighter fraction contains above about 75 percent of the benzene, toluene and ethylbenzene found in the said lighter boiling material.
3. A process in accordance with claim 1 wherein essentially all the said lighter fraction is not recycled into the process streams.

4. A process in accordance with claim 1 wherein the heavy residue is cracked at a temperature sufficient to produce significant quantities of benzene and/or toluene and ethylbenzene.

5. A process in accordance with claim 1 wherein the improvement further comprises the said lighter fraction including materials which deleteriously affect the quality of phenol as measured by the sulfonation color test.

6. A process in accordance with claim 5 wherein the said lighter fraction contains above about 75 percent of the benzene, toluene, ethylbenzene and materials which deleteriously affect the quality of phenol as measured by sulfonation color test found in the said lighter boiling material.

7. A process in accordance with claim 5 wherein essentially all the said lighter fraction is not recycled into the process streams.

8. A process in accordance with claim 5 wherein the heavy residue is cracked at a temperature sufficient to produce significant quantities of benzene and/or toluene and ethylbenzene.

* * * * *